(12) United States Patent
McHugh et al.

(10) Patent No.: US 6,289,113 B1
(45) Date of Patent: Sep. 11, 2001

(54) HANDHELD IRIS IMAGING APPARATUS AND METHOD

(75) Inventors: James Timothy McHugh, Newark, DE (US); James Henry Lee, Mt. Laurel; Cletus Bonaventure Kuhla, Tabernacle, both of NJ (US)

(73) Assignee: Iridian Technologies, Inc., Moorsetown, NJ (US)

( * ) Notice: Subject to any disclaimer, the term of this patent is extended or adjusted under 35 U.S.C. 154(b) by 0 days.

(21) Appl. No.: 09/200,214

(22) Filed: Nov. 25, 1998

(51) Int. Cl.⁷ ........................................... G06K 9/00
(52) U.S. Cl. ................................. 382/117; 351/218
(58) Field of Search ........................... 382/117, 115, 382/218; 351/218, 221

(56) References Cited

U.S. PATENT DOCUMENTS

| | | | |
|---|---|---|---|
| 4,641,349 | 2/1987 | Flom et al. | 382/2 |
| 4,876,608 | 10/1989 | Eaton | 358/443 |
| 5,106,183 * | 4/1992 | Yoder, Jr. | 351/212 |
| 5,151,583 | 9/1992 | Tokunaga et al. | 250/201.2 |
| 5,187,506 * | 2/1993 | Carter | 351/221 |
| 5,291,560 | 3/1994 | Daugman | 382/2 |
| 5,359,669 | 10/1994 | Shanley et al. | 382/6 |
| 5,404,163 | 4/1995 | Kubo | 348/142 |
| 5,572,596 | 11/1996 | Wildes et al. | 382/117 |
| 5,581,630 | 12/1996 | Bonneau, Jr. | 382/116 |
| 5,629,981 | 5/1997 | Nerlikar | 380/25 |
| 5,646,709 * | 7/1997 | Carter | 351/218 |
| 5,717,512 * | 2/1998 | Chmielewski | 359/210 |
| 5,719,950 | 2/1998 | Osten et al. | 382/115 |
| 5,751,260 | 5/1998 | Nappi et al. | 345/8 |
| 5,751,836 | 3/1998 | Wildes et al. | 382/117 |
| 5,901,238 * | 5/1999 | Matsushita | 382/117 |
| 5,956,122 * | 9/1999 | Doster | 382/117 |

FOREIGN PATENT DOCUMENTS

| | | |
|---|---|---|
| 97302580 | 4/1997 | (EP) . |
| 9611787 | 6/1996 | (GB) . |
| 9621900 | 10/1996 | (GB) . |
| WO 97/21188 | 6/1997 | (WO) . |
| WO 97/46978 | 12/1997 | (WO) . |
| WO 97/46979 | 12/1997 | (WO) . |
| WO 97/46980 | 12/1997 | (WO) . |
| WO 98/08439 | 3/1998 | (WO) . |
| WO 98/32093 | 7/1998 | (WO) . |

\* cited by examiner

Primary Examiner—Joseph Mancuso
(74) Attorney, Agent, or Firm—Woodcock Washburn Kurtz Mackiewicz & Norris LLP

(57) ABSTRACT

A compact, handheld imaging apparatus which can be used to capture high-quality iris images for identification of a person. The handheld iris imager is non-invasive and non-contacting and comprises a camera, a cold mirror, a lens, and an illuminator. The imager has sensors and indicators which assist a user in aligning and focusing the device. The imager also automatically captures the image when proper positioning is achieved. A template representative of the iris features is extracted and then compared to a database of previously stored templates to identify the person.

25 Claims, 6 Drawing Sheets

HANDHELD IRIS IMAGING APPARATUS AND METHOD

FIELD OF THE INVENTION

The present invention relates in general to identification of physical characteristics of a human being or other animal. More particularly, the present invention relates to iris recognition.

BACKGROUND OF THE INVENTION

Various technologies are used for uniquely identifying a person in accordance with an examination of particular attributes of either the person's interior or exterior eye. One of these technologies involves the visual examination of the particular attributes of the exterior of the iris of at least one of the person's eyes. The iris of the human eye has random patterns of striations, ciliary processes, crypts, rings, furrows and other features which had been shown capable of generating highly unique biometric templates for personal identification. In this regard, reference is made to U.S. Pat. No. 4,641,349, "Iris Recognition System", issued to Flom et al., and U.S. Pat. No. 5,291,560, "Biometric Personal Identification System Based on Iris Analysis", issued to Daugman. As made clear by these patents, the visible texture of a person's iris can be used to distinguish one person from another with great accuracy. Thus, iris recognition can be used for such purposes as controlling access to a secure facility or a bank automatic teller machine, for example. An iris recognition system involves the use of an imager to video image the iris of each person attempting access, and image processing means for comparing this iris video image with a reference iris image on file in a database.

Iris identification systems have been developed that are capable of collecting images of the iris and processing them to produce biometric templates. These templates may be used to identify individual irises with extremely low error rates, on the order of 1 in $10^{78}$. The systems capture the iris images using stationary optical platforms that are often large, complex, and expensive. The systems are difficult to use with minimal cooperation of the subject being identified. As a result their usefulness in many applications is limited.

Although the art of human recognition systems is well developed, there remain some problems inherent in this technology, particularly the lack of a portable or handheld device specifically designed to solve the problems inherent in capturing a close-up, high-quality, properly focused image of the iris of the eye. Therefore, a need exists for a recognition system that overcomes the drawbacks of the prior art.

SUMMARY OF THE INVENTION

The present invention is directed to a handheld iris imaging apparatus for obtaining an image of an iris of an eye, comprising: iris acquisition means having a front surface; a lens having a image plane disposed in front of the front surface of the iris acquisition means; a mirror disposed on a side of the lens opposite the iris acquisition means; and an illuminator disposed along a side of the mirror.

According to one aspect of the invention, the iris acquisition means comprises a camera, and the mirror is a cold mirror. The camera is sensitive to light having a wavelength in a range between about 400 nm and about 1100 nm. The mirror reflects light having a wavelength in a range between about 400 nm and about 700 nm and passes light having a wavelength greater than about 700 nm.

According to a further aspect of the invention, the illuminator emits light having a wavelength in a range between about 680 nm and about 900 nm towards the iris of the eye being imaged, the eye being out of contact with the iris imaging apparatus.

According to a further aspect of the invention, the iris imaging apparatus further comprises at least a visible indicator or an audible indicator to indicate when the image of the iris has been obtained.

A further embodiment within the scope of the present invention is directed to a method of obtaining an iris image of a subject, comprising the steps of: (a) illuminating an iris of the subject; (b) forming an approximately centered image of the iris at an image plane of a camera; (c) storing the image in a memory; (d) determining if the image is an image of sufficient quality; and (e) repeating steps (a) through (d) until the image of sufficient quality is obtained.

According to one aspect of the invention, the method further comprises the step of activating an indicator if the image is of insufficient quality. The indicator is an audible indicator.

According to one aspect of the invention, the method further comprises the step of activating an indicator if the image is of sufficient quality. The indicator is a visible indicator.

According to a further aspect of the invention, the method further comprises the step of displaying the image on a display.

A further embodiment within the scope of the present invention is directed to a system of identification, comprising: a handheld imaging apparatus; a first memory for storing at least one template of at least one image of an iris of at least one person's eye; a second memory for storing a template of an iris image obtained by the iris acquisition means; and a comparator for comparing the template of the iris image of the second memory with the at least one stored template of the first memory to identify the person.

According to one aspect of the invention, the iris acquisition means comprises a camera, and the mirror is a cold mirror.

According to another aspect of the invention, the comparator comprises a processor responsive to an output of the camera for comparing the template of the second memory with the at least one stored template of the first memory.

According to another aspect of the invention, the first memory, the second memory, and the comparator are disposed in a housing that is separate from the handheld iris imaging apparatus. In an embodiment, the housing is coupled to the handheld iris imaging apparatus by a wireless modem.

According to another aspect of the invention, the system further comprises at least one of a visible indicator and an audible indicator disposed within the handheld iris imaging apparatus.

According to another aspect of the invention, the system further comprises a focus assessment processor coupled to the at least one of a visible indicator and an audible indicator.

According to another aspect of the invention, the system further comprises a display disposed within the handheld iris imaging apparatus.

A further embodiment within the scope of the present invention is directed to a method of identification of a person, comprising the steps of: (a) storing image information of the iris of at least one person's eye; (b) illuminating an eye of an unidentified person having an iris; (c) obtaining an image of the iris of the unidentified person; (d) storing the image in a memory; (e) determining if the image is an image of sufficient quality for a step (g) of comparing; (f) repeating steps (b) through (e) until the image of sufficient quality is obtained; and (g) comparing a template of the obtained image with the stored image information to identify the unidentified person.

According to an aspect of the present invention, the method further comprises the step of activating an indicator if the image is of insufficient quality. The indicator is an audible indicator.

According to an aspect of the present invention, the method further comprises the step of activating an indicator if the image is of sufficient quality. The indicator is a visible indicator.

According to another aspect of the present invention, the step of determining if the image is an image of sufficient quality comprises the step of focus assessment processing the image.

According to another aspect of the present invention, the method further comprises the step of displaying the image on a display.

BRIEF DESCRIPTION OF THE DRAWINGS

The foregoing and other aspects of the present invention will become apparent from the following detailed description of the invention when considered in conjunction with the accompanying drawings. For the purpose of illustrating the invention, there is shown in the drawings an embodiment that is presently preferred, it being understood, however, that the invention is not limited to the specific methods and instrumentalities disclosed. In the drawings.

DESCRIPTION OF EXEMPLARY EMBODIMENTS AND BEST MODE

The present invention is directed to a compact, handheld imaging apparatus and method which can be used to capture high-quality iris images. Preferably, the imager has sensors and indicators which assist the human operator in aligning and focusing the device. The imager also automatically captures the image when proper positioning is achieved. Because it is small and compact, it is practical for use as an accessory to a personal computer, and for many business and consumer applications where cost is critical. Throughout the following detailed description similar reference numbers refer to similar elements in the figures of the drawings.

Figure 1:
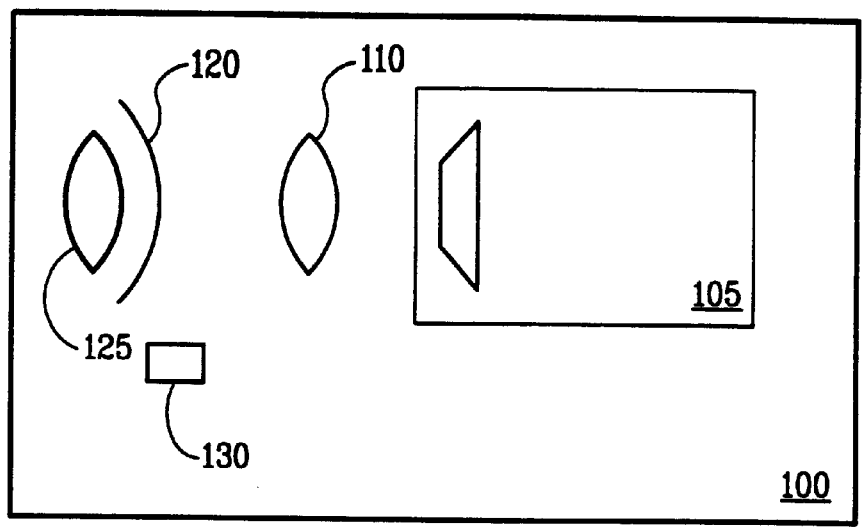
FIG. 1 is a schematic diagram of an exemplary iris imager in accordance with the present invention.

FIG. 1 illustrates a preferred embodiment of the handheld imager 100 in accordance with the present invention. The exemplary handheld, non-invasive, non-contacting iris imager comprises iris acquisition means 105, an imaging lens 110, a mirror 120, an optional diopter correction lens 125, and an illuminator 130. The imager 100 can be powered by a standard DC or AC supply, and preferably a 9 volt battery (not shown).

The iris acquisition means 105 is preferably a conventional solid state video camera, such as a charged coupled device (CCD) or complementary metal oxide semiconductor (CMOS) device. A preferred camera is a ⅓ inch format, monochrome CCD board camera, such as Computar Model EM200. Preferably, the video camera 105 is sensitive to light of wavelengths in the range of about 400 nanometers to about 1100 nanometers, and is positioned so that its front surface coincides with the image plane of the lens 110 in front of it. In the preferred embodiment, the object plane of the lens is approximately 89 mm in front of the lens 110 . More preferably, the lens 110 is an optical lens with approximately 14.2 mm focal length.

The mirror 120, preferably a concave cold mirror having a radius of curvature preferably about 276 mm, is disposed on the side of the lens 110 opposite the video camera 105 and creates a magnified virtual image of the iris behind the mirror 120. In the preferred embodiment, the mirror 120 reflects visible light with wavelengths in the range of about 400 to about 700 nanometers, and passes light having longer wavelengths, such as those in the range of about 700 to about 900 nanometers.

The illuminator 130 is positioned just outside the edge of the cold mirror 120 and is used to illuminate the iris of the subject being identified. The preferred illuminator 130 emits light having wavelengths of about 680 to about 900 nanometers. Preferably, the illuminator 130 is a miniature quartz halogen or krypton gas bulb operating at approximately 1 watt.

The imager acquires images of an iris with sufficient clarity, focus, and size for use with conventional image processing and comparison routines. A preferred image processing and comparison routine is described in U.S. Pat. No. 5,291,560, "Biometric Personal Identification System Based on Iris Analysis", issued to Daugman, and commonly assigned with the present invention to IriScan Inc., and incorporated herein by reference. However, any processing and comparison technique can be used with the image that is acquired at the imager, such as the image pixel correlation technique described in U.S. Pat. No. 5,572,596, "Automated, Non-Invasive Iris Recognition System and Method", issued to Wildes et al. and the techniques described in U.S. Pat. No. 4,641,349, "Iris Recognition System", issued to Flom et al., both of which are incorporated herein by reference.

Figure 2A:
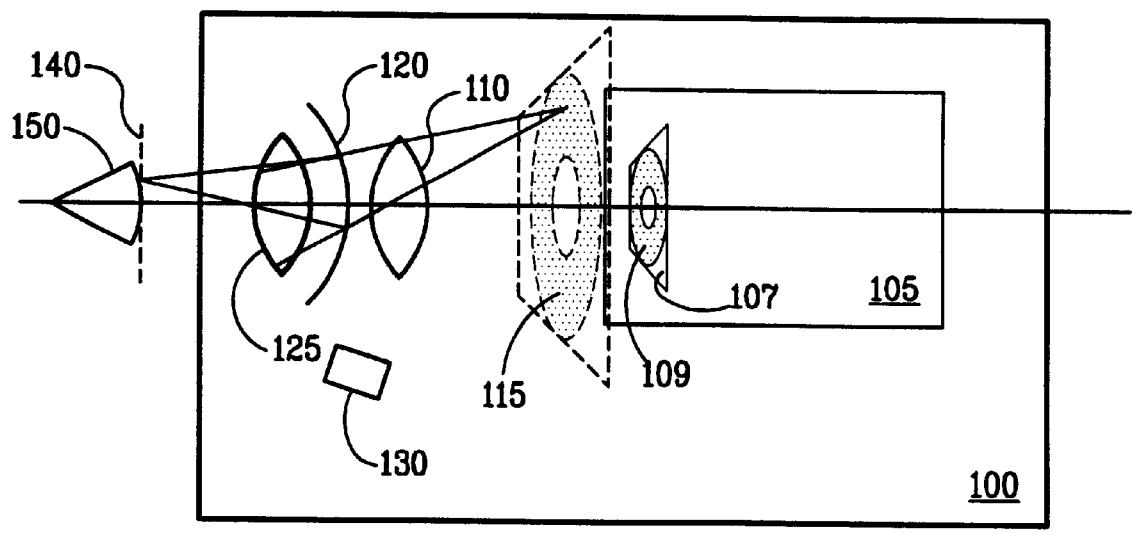
FIG. 2A is a schematic diagram of the imager of FIG. 1 shown in greater detail.

FIG. 2A shows the apparatus of FIG. 1 in greater detail. The lens 110 gives a high resolution image of the eye 150 of the user, who is positioned in front of the lens 110, so that extreme proximity between the eye 150 and the imager 100 is not required (i.e., no contact is needed between the subject and the imager 100).

The handheld iris imager comprises a solid-state image capture device and an optical system which forms an image 109 of the iris on the image capture device at the image plane of the video camera 105 and at the same time produces a virtual image 115 of the iris which the user can use to position and focus the iris image. As a result, the user can, using the same eye being imaged, see a reflected image of the iris which can be used to position the handheld imager 100 so that a good iris image (i.e., an image that can be processed and compared to those stored in a database) can be obtained.

FIG. 2A also shows an optional dioptric correction lens 125 positioned between the eye 150 and the cold mirror 120. The dioptric correction lens 125 is an adjustable optical element which corrects for the close-range focusing ability of the individual eye, which varies from subject to subject. When the lens 125 is properly adjusted, the magnified, reflected virtual image 115 of the subject's eye appears in sharp focus to the subject at the same eye-to-mirror distance at which the subject's eye is sharply focused on the front surface of the camera. This simplifies use of the imager, because the subject simply positions the image so that the virtual image 115 of the iris appears sharply focused.

A preferred embodiment of the dioptric correction mechanism has no correction lens 125 and instead has a mechanical means (not shown) for adjusting the position of the cold mirror 120 relative to the camera lens 110. This allows the user to vary the object distance of the cold mirror 120, thus changing the eye-to-lens distance at which the virtual image 115 of the iris is sharply focused.

The ability to set the dioptric correction mechanism to accommodate a particular user has a great utility if the imager is used by only one person most of the time. Once the correction is set, the user can easily position the device to obtain a sharply focused reflected image. This automatically produces a sharply focused image from the camera and substantially immediate acceptance of the image by the focus assessment processor described below. Image capture time is thereby reduced and overall convenience and utility is enhanced.

An eye 150 is positioned in front of the imager 100 (e.g., about 3.5 inches in front), as shown in FIG. 2A, and the illuminator 130 is turned on. This, in turn, illuminates the eye 150 and the iris therein. Preferably, the light having wavelengths of about 400 to about 700 nanometers is reflected by the cold mirror 120, thereby forming a magnified virtual image 115 behind the mirror 120 which the user can see through the eye being imaged. The radius of curvature of the mirror is selected so that the magnified image 115 of the eye substantially fills the user's entire field of view. Hence, when the imager 100 is positioned so that the entire eye 150 is visible, it is virtually assured that the eye 150 will be substantially centered in the object plane 140 of the camera 105. Under these conditions, the light having wavelengths of about 700 to about 900 nanometers is passed by the mirror 120 and forms an approximately centered image 109 of the eye 150 at the image plane 107 of the camera 105. The image is then captured and processed, as described below.

Although a cold mirror (one which reflects shorter wavelengths and passes longer wavelengths) is described herein, it is understood that a hot mirror (one which reflects longer wavelengths and passes shorter wavelengths) could also be used in accordance with the present invention. Such a configuration is shown in an imager 101 in FIG. 2B. The eye 150 is illuminated by an illuminator 131 emitting light having wavelengths in the range of about 680 to 900 nanometers. This light is reflected by the eye 150 and the light having wavelengths in the range of about 700 to 900 nanometers is reflected by the hot mirror 121 to be focused by the lens 111 onto the front surface of the camera 106. Light reflected from the eye 150 having shorter (visible) wavelengths in the range of about 400 to 700 nanometers passes through the hot mirror 121 and strikes a concave broadband mirror 122 which reflects light having wavelength from about 400 to 900 nanometers. This light forms a virtual image 115 of the eye 150 behind the concave mirror 122 that the user can see and use to align and focus the device, as described below.

Figure 3:
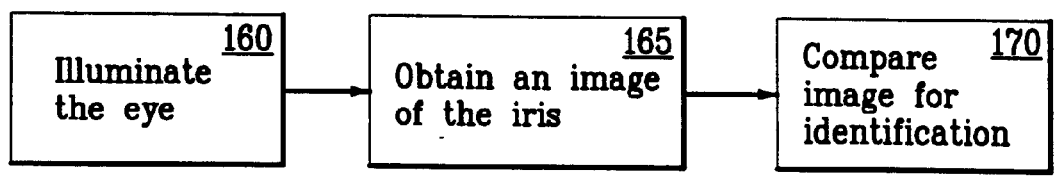
FIG. 3 is a simplified flowchart of a method of operation in accordance with the present invention.
Figure 2B:
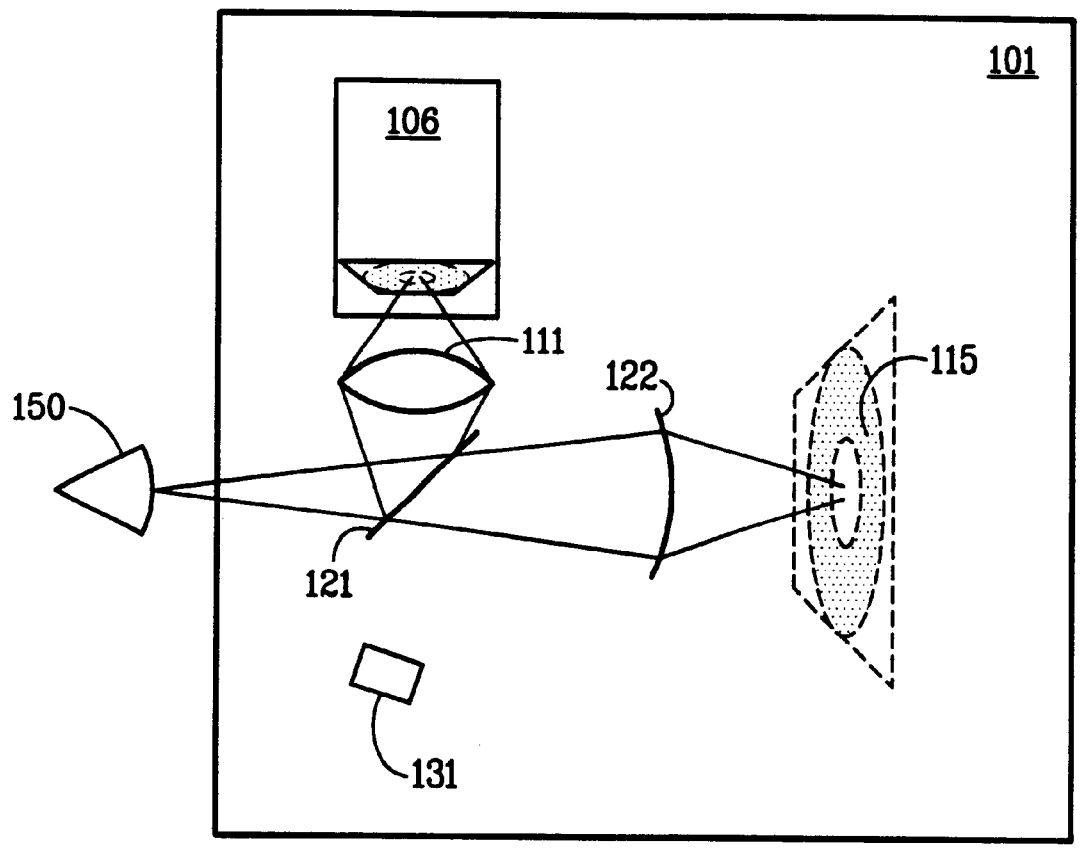
FIG. 2B is a schematic diagram of another exemplary imager in accordance with the present invention.

The imager 100 of FIGS. 1 and 2A, as well as the imager of FIG. 2B, is used in a system to identify the iris image that has been captured. As shown in FIG. 3, the eye is illuminated at step 160, an acceptable or suitable image of the iris is obtained at step 165, and the image (or a template of the image) is compared to pre-existing images (or to pre-existing templates) in a memory or database for identification of the subject at step 170. The system processes the image and compares it to stored images (or templates) to identify the iris, and thus, the user. In accordance with one embodiment of the present invention, image processing algorithms are used to extract a fixed length template (e.g., about 512 bytes long) from each iris image. Iris images are compared by determining the percentage of bits in each template that match. If the percentage of bits that match exceeds a predetermined threshold (e.g., 75%), then it is determined that the iris images being compared belong to the same iris, thereby identifying the subject being tested.

Figure 4:
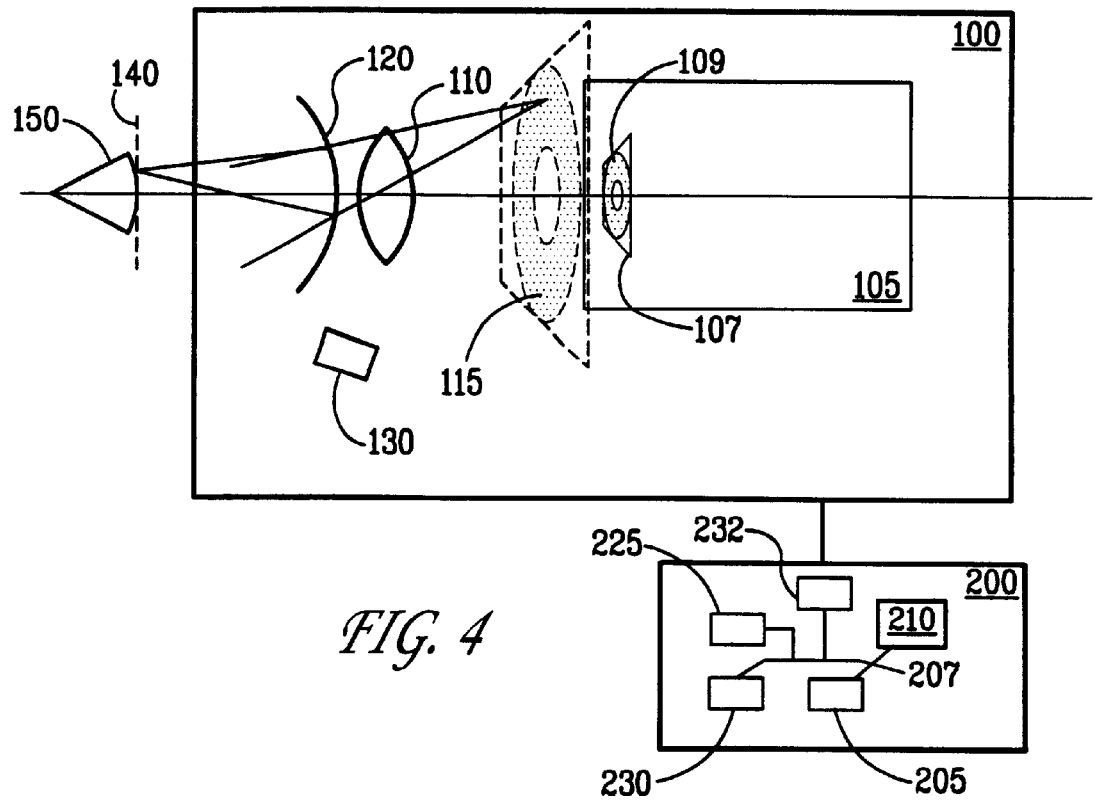
FIG. 4 is a schematic diagram of an exemplary iris image recognition system in accordance with the present invention.

FIG. 4 is a schematic diagram of an exemplary iris image recognition system in accordance with the present invention. The imager 100 is coupled to a microprocessor 210 that performs the processing and comparison. The microprocessor 210 can reside in a conventional computer 200, such as a standard personal computer (e.g., 100 MHZ, 32 Mbyte DRAM, monitor, keyboard, ports, hard drive, floppy drive, CD-ROM drive), as shown, or within an IrisEngine manufactured by IriScan Inc., Marlton, N.J.

The microprocessor 210 is coupled to the imager 100 via conventional cables and/or printed circuit boards (PCBs) that are connected into slots on the computer such as an ISA slot or a PCI slot. Other conventional means for coupling the imager 100 and the microprocessor 210 can be employed. The microprocessor 210 controls the imager 100 and runs software held in read only memory (ROM) 205. The processor 210 is connected via a bus 207 to the ROM 205, a random access memory (RAM) 232, another memory such as an erasable programmable ROM (EPROM) 230, and an input/output (I/O) controller 225. The RAM 232 is large enough to hold at least one captured image of an iris. The I/O controller 225 is connected to the appropriate circuitry and drivers (not shown) for issuing commands to control the imager 100.

The imager 100 preferably transmits the images in RS170 format to a frame grabber PCB, such as the PixLink VGX2MB frame grabber PCB, for image processing; or provides the digital images directly to the processing unit 210. "On/off" data is transmitted from the imager 100 to the processor 210 to initiate the image acquisition function. A digital image could be provided if a digital camera is used. Preferably, for an analog video camera, data is analog RS170 from the camera 105 to the frame grabber PCB, or digital from a digital camera to the microprocessor 210, and digital for all other functions.

The image processing consists of a number of image processing steps (such as those described in U.S. Pat. No. 5,291,560 and U.S. Pat. No. 5,572,596, which are herein incorporated by reference) which lead to extraction of a unique and highly specific digital biometric template that can be used to identify the individual based on intensity patterns within the iris. The biometric template is then compared against other templates or images stored in a memory (such as a RAM or EPROM) 230 within the computer 200. The memory 230 stores selected data representing images of the iris of a plurality of subjects. A match of the biometric template with a template stored in the memory 230 identifies the subject whose iris is being imaged.

Figure 5:
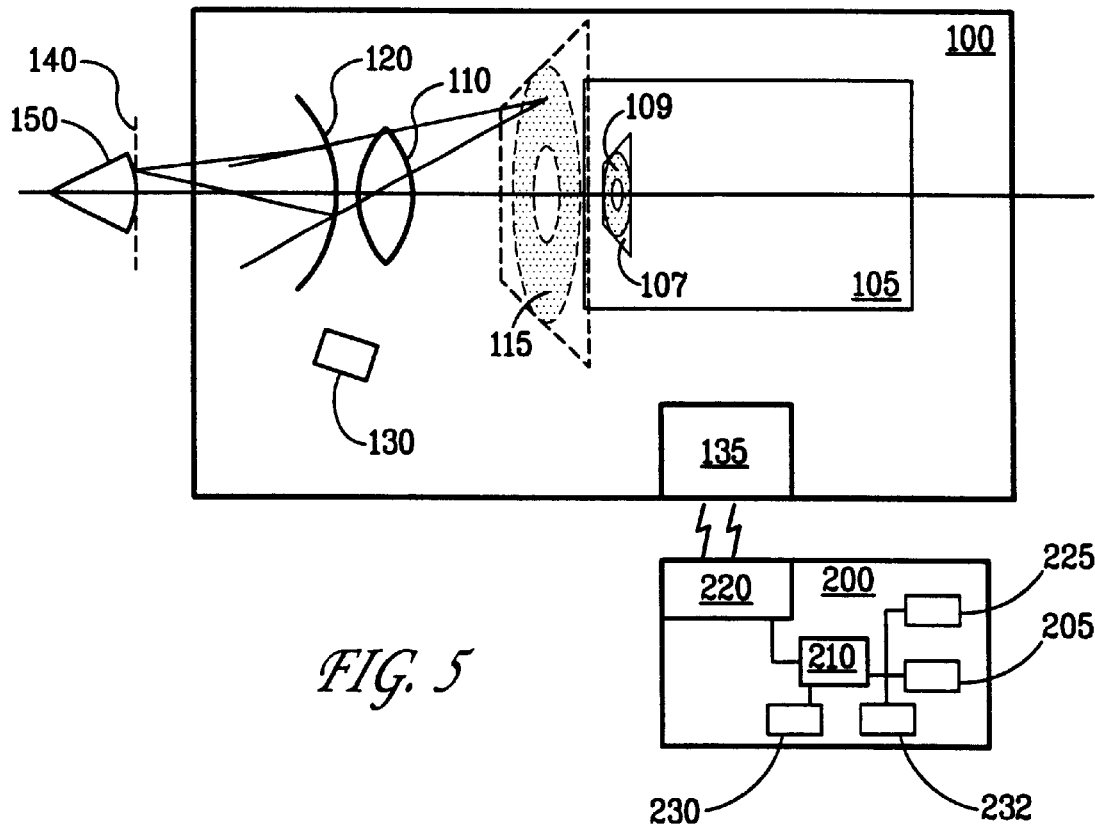
FIG. 5 is a schematic diagram of another exemplary iris image recognition system in accordance with the present invention.

As shown in FIG. 5, the imager 100 can be linked to the microprocessor 210 via wireless means, such as an RF modem 135 residing within the imager 100 communicating with a companion modem 220 on the microprocessor 210 or elsewhere within in the computer 200. This increases the flexibility of the imager 100 for certain applications where the limited range of motion imposed by a wired connection would limit its usefulness. These might include, for example, certain applications such as medical or corrections facilities where it is not desirable or convenient to bring the individual whose eye is being imaged close to the external computer 200. The modem 135 also can receive instructions from the computer 200, such as to illuminate the lamp 130, or activate visible and/or audible indicators (described below with respect to FIG. 6).

Although an image of the eye is reflected back to the subject in mirror 120, this may not provide the desired feedback to the user to enable the user to properly position the imager so that a suitable iris image is obtained. For example, a user may be a novice in using and positioning the imager 100 with respect to the eye 150, or the user may be attempting to image the eye of another subject with the imager. Thus, preferably, the imager 100 comprises a passive feedback mechanism to guide the user in positioning the eye 150 to an optimum location to allow acquisition of a suitable image.

Figure 6:
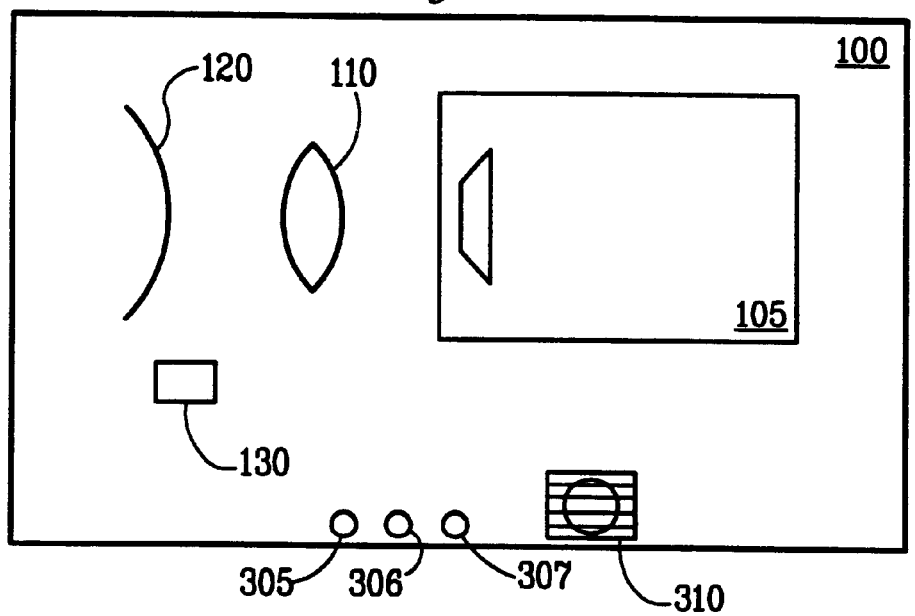
FIG. 6 is a schematic diagram of an exemplary iris imager having visual and aural indicators in accordance with the present invention.

The passive feedback mechanism is an indicator or combination of indicators that provides, on a near real-time basis, an indication to the user that an adequate iris image has or has not been obtained. FIG. 6 is a schematic diagram of an exemplary iris image recognition system that includes position indicators in accordance with the present invention. Preferably, the indicator is visible and/or audible, such as, for example, an indicator lamp 305 (e.g., a light emitting diode (LED)) that lights when an acceptable image has been captured (i.e., "image acquired"), and a aural indicator via a speaker 310, such as a beep or other tone, that sounds periodically until an acceptable image has been captured (i.e., "imaging in progress").

Additional indicators 306, 307 can be also be used, either alone or in combination, for such indications as "subject identified—accept" and "subject not identified—reject". These indications would be activated pursuant to the results of the processing and comparison performed at the microprocessor 210, as described above with respect to FIG. 4.

The imager 100 also preferably has an on/off switch (not shown), such as a pushbutton, for powering up the imager and initiating the image acquisition process. Power for the imager 100 is preferably supplied by a battery, but can also be supplied externally, such as, for example, from the computer 200 comprising the microprocessor 210. The imager 100 receives and acts on instructions from the processor 210 to perform functions such as lighting or turning off the indicator lamp(s) 305, providing the audible signals via the speaker 310, and lighting the 'accept' and 'reject' indicators.

It should be noted that the imagers of FIGS. 4, 5, and 6 can also contain the optional dioptric correction lens 125, described above with respect to FIG. 2A.

Figure 7:
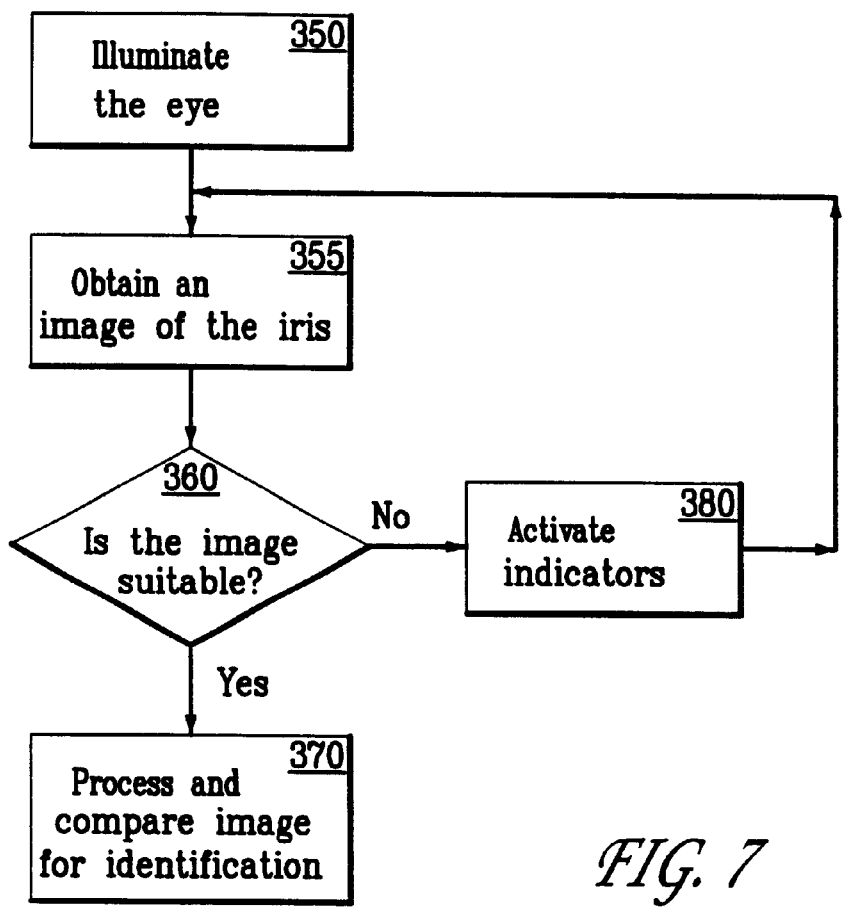
FIG. 7 is a more detailed flow chart of a method of operation in accordance with the present invention.

FIG. 7 is a more detailed flow chart of a method of operation in accordance with the present invention. The eye is illuminated at step 350 and an image of the iris is obtained at step 355. At step 360, it is determined if the image is suitable for use with the image processing and comparison routines. If the image is suitable, the image is passed to the processor for further processing and comparison, at step 370. If the image is not suitable, at step 380, the indicator(s) is activated (e.g., a beep sound is issued), and processing continues at step 355 (i.e., another image is obtained).

Figure 8:
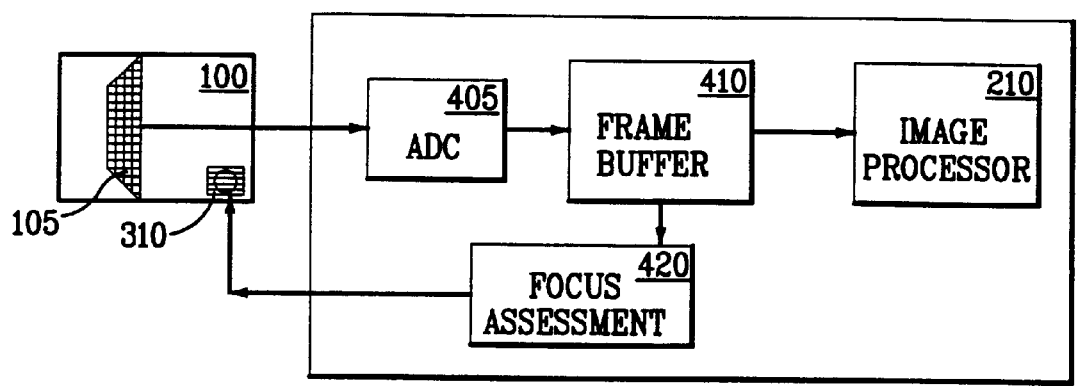
FIG. 8 is a schematic diagram of an exemplary iris image recognition system having a focus assessment processor in accordance with the present invention.

Because the eye's own focusing system automatically adjusts to bring the virtual image 115 into sharp focus to the user, it cannot be relied upon to always accurately focus the eye image on the camera 105. For this purpose, an external focus assessment system is used in one embodiment, as shown in FIG. 8. Video image information from the hand-held imaging device 100 is received as an analog video signal which conforms to a standard format such as NTSC or PAL. In these formats video frames are transmitted at a rate of 25 (PAL) or 30 (NTSC) frames per second. The analog image data is transmitted to an analog-to-digital converter 405 and stored in a frame buffer memory 410, such as a RAM similar to RAM 232 described above with respect to FIG. 4, and capable of storing one complete frame of digitized video information. A focus assessment processor 420 accesses the digitized image information and applies certain measurement algorithms which are disclosed in a co-pending application entitled "Video-Rate Focus Assessment", filed concurrently with this application (Attorney Docket No. ICAN-0067), and incorporated herein by reference. The output of the focus assessment is used to control an indicator, such as the audible indicator 310. As long as the focus assessment processor 420 determines that the captured image is not acceptable for further processing and comparison, the audible indicator 310 is directed to emit periodic sounds to alert the user. Images are repeatedly acquired and assessed until an acceptable one is received. After an acceptable iris image has been received, the audible indicator 310 is turned off and the final image is retained for further processing and comparison, for example, by the microprocessor 210, as described above. Any known technique for image focusing can be used with the imager of the present invention, such as those described in U.S. Pat. No. 4,876,608, entitled "Focus and Signal to Noise Measurement Routines in Input Scanners", issued to Eaton, U.S. Pat. No. 5,151,583, entitled "Focus Adjustment Device Having Restricting Means for Restricting a Selecting Action According to the Degree of Nearness of a Distance Measurement", issued to Tokunaga et al., and U.S. Pat. No. 5,404,163, entitled "In-Focus Detection Method and Method and Apparatus Using the Same for Non Contact Displacement Measurement", issued to Kubo. The preferred system and method for focus assessment is described below.

A focus score is computed for each video frame (i.e., each captured image). If the focus score exceeds a predetermined value, then it is determined that the image is focussed enough for further processing and comparison. If the focus score does not exceed the predetermined value, then it is determined that the image is not focussed enough for further processing, and an indicator (such as indicator 310, described with respect to FIG. 6) is activated and a further image is captured. Alternatively, a sequence of image frames can be obtained that cycle through a range of focus distances strobed at the video frame-rate, and the focus score computed for each frame can enable the selection of the best focused frame within the sequence of frames. For example, by obtaining image frames at each of several different lens settings and then fitting a spline curve to their respective focus scores one can predict the lens position that would deliver substantially the sharpest focus, by setting the derivative of the parameterized spline curve to zero and then solving the equation for position.

Specific implementation features of the preferred focus assessment system and method which enable its real-time operation, include (1) the computation of quantities in the 2D Fourier domain, without needing to compute an actual 2D Fourier Transform of an image (this avoids the need for approximately 2.25 million floating-point operations required for an FFT (Fast Fourier Transform) on a 500×500 pixel image, as the computational complexity of an FFT on nxn data is $O(n^2 \log_2 n)$); (2) only 6,400 integer multiplications (squarings) are performed, which in turn can be eliminated altogether by using small look-up tables; (3) no floating-point operations are required; (4) computation of focus scores is based upon simple algebraic combinations of pixel values within local closed neighborhoods, repeated across regions of the image; and (5) these operations not only allow the algorithm to execute in real-time, but it also enables a straightforward implementation in simple, low-cost, hardware devices that could be embedded within a digital camera or frame grabber.

Preferably, the focus assessment processor 420 is fast enough to determine a focus score for each frame in a video image stream in less than the time it takes to acquire a new frame (e.g., approximately 25 ms). The frame-by-frame focus scores can be used to control a moving lens element for rapid and accurate focus control, or alternatively, to select which of several frames in a video stream is the one in best focus. The rapid selection of well-focused video frames for further processing, such as image analysis and pattern recognition, is important in real-time computer vision because it prevents wasting processing time on poorly-focused images.

The preferred focus assessment processor measures the focus quality of video images at standard rates of 25 (PAL) or 30 (NTSC) frames per second.

It is contemplated that the focus assessment processor 420 can be implemented in a general purpose personal computer (PC) or by a dedicated, low cost processor which is small enough to be incorporated into the camera electronics.

The processing of a video frame results in the return of an integer value (on a scale between 0 and 100) reflecting the quality of focus; the larger the value of the integer, the better the focus. A value of 0 indicates a completely defocused image whereas the value of 100 indicates maximum focus quality. A predetermined threshold is used to determine whether an image is sufficiently focused or whether another image needs to be retrieved. For example, values greater than about 40 can indicate sufficient quality of focus to warrant further image processing, while values less than about 40 cause a new image frame to be grabbed, and optional feedback provided to the focusing mechanism, if one exists, or to the subject controlling the camera position (via the indicator 310, for example).

Optical defocus is a phenomenon of the 2D Fourier domain. An image represented as a 2D function of the real plane, I(x,y), has a 2D Fourier Transform F($\mu$, v) defined as shown in equation 1.

$$F(\mu, v) = \frac{1}{(2\pi)^2} \int_x \int_y I(x, y) e^{i(\mu x + vy)} dx dy \quad (1)$$

In the image domain, defocus is preferably represented as convolution by the 2D point-spread function of the defocused optics. This in turn may be modeled as a Gaussian whose space constant is proportional to the degree of defocus. Thus, for perfectly focused optics, the optical point-spread function shrinks almost to a delta function, and convolution with a delta function causes no change to the image. Progressively defocused optics equates to convolving with a wider and wider point-spread function, which averages together whole neighborhoods of pixels by such a weighting function, thereby producing an increasingly blurred image.

If the convolving optical point-spread function causing defocus is modeled as a Gaussian whose width represents the degree of defocus, then defocus is equivalent to multiplying the 2D Fourier Transform of a perfectly focused image with the 2D Fourier Transform of the "defocusing" (convolving) Gaussian. This latter quantity is itself just another 2D Gaussian but in the Fourier domain, and its space constant ($\sigma$) there is the reciprocal of that of the image-domain convolving Gaussian that represented the optical point-spread function. The preferred focus assessment processor uses (1) the duality of convolution and multiplication in the two domains; (2) the fact that a Gaussian has a Fourier Transform which is itself a Gaussian, but with the reciprocal width because of (3) the Similarity Theorem. Thus, the 2D Fourier Transform $D_\sigma(\mu,v)$ of an image defocused to degree $\sigma$ is related to F($\mu$,v), the 2D Fourier Transform of the corresponding in-focus image, as given by equation 2.

$$D_\sigma(\mu, v) = e^{-\left(\frac{\mu^2 + v^2}{\sigma^2}\right)} F(\mu, v) \quad (2)$$

From the above equation, the effect of defocus is to attenuate primarily the highest frequencies in the image, and that lower frequency components are virtually unaffected by defocus since the exponential term approaches unity as the frequencies ($\mu$,v) become small. For simplicity, the present description has assumed isotropic optics and isotropic blur, and the optical point-spread function has been described as a Gaussian. However, the analysis can readily be generalized to non-Gaussian and to anisotropic optical point-spread functions.

Thus, an effective way to estimate the quality of focus of an image is to measure its total amount of energy in the 2D Fourier domain at high spatial frequencies, since these are the most attenuated by defocus. One may also perform a kind of "contrast normalization" to make such a spectrally-based focus measure independent of image content, by comparing the ratio of energy in the highest frequency bands to that in slightly lower frequency bands. Such spectrally-based energy measurements are facilitated by exploiting Lord Rayleigh's theorem for conserved total power in the two domains, shown in equation 3.

$$\int_{-\infty}^{+\infty} \int_{-\infty}^{+\infty} |I(x, y)|^2 dx dy = \int_{-\infty}^{+\infty} \int_{-\infty}^{+\infty} |F(\mu, v)|^2 d\mu dv \quad (3)$$

Thus, high-pass filtering or band-pass filtering an image at a ring of high spatial frequency (using only convolution in the 2D image domain) and measuring the residual energy, is equivalent to making the corresponding energy measurement in the high frequency bands of the 2D Fourier domain. The appropriate measurements in the 2D Fourier domain to assess focus can be performed without computing a time-consuming 2D Fourier Transform. Indeed, the measurements can be performed without even a single floating-point operation, and even without any multiplications if appropriate convolution kernels and look-up tables are used.

A real-time procedure for focus assessment based on these theoretical principles is used in the focus assessment processor 420. It executes much faster than the video frame-rate, and so real-time focus assessments can be made on a frame-by-frame basis. These can be used either to control the position of a focusing lens element, or alternatively as a type of autofocus system in which frames are grabbed at a variety of focal depths in order to select only the best one for processing, or to prevent time being wasted on processing image frames which are assessed to be in poor focus.

The 2D spectral measurements described above can be implemented by convolving an image with the following convolution kernel, in which pixel values within a predetermined region, such as, for example, an (8×8) neighborhood, are added together with the weights indicated in each of the cells:

| -1 | -1 | -1 | -1 | -1 | -1 | -1 | -1 |
|----|----|----|----|----|----|----|----|
| -1 | -1 | -1 | -1 | -1 | -1 | -1 | -1 |
| -1 | -1 | +3 | +3 | +3 | +3 | -1 | -1 |
| -1 | -1 | +3 | +3 | +3 | +3 | -1 | -1 |
| -1 | -1 | +3 | +3 | +3 | +3 | -1 | -1 |
| -1 | -1 | +3 | +3 | +3 | +3 | -1 | -1 |
| -1 | -1 | -1 | -1 | -1 | -1 | -1 | -1 |
| -1 | -1 | -1 | -1 | -1 | -1 | -1 | -1 |

It should be noted that no pixel-by-pixel multiplications are needed in order to impose these weights. Rather, the pixels in the central region are added together, such as the (4×4) square, that sum is tripled, and then all pixel values in the outer two pairs of rows and columns are subtracted from the tripled sum. The result is squared and added to an accumulator, thus implementing the left-hand side of equation (3) above for this local region of the image. The complete (8×8) convolution kernel is then moved to a new position in the image, along a sampling grid that selects every 4th row and every 4th column, and the operation is repeated. Thus, to assess the quality of focus within the central (320×320) region of an image, this set of 64 pixel summations followed by a squaring operation is repeated a total of $(320/4)^2 = 6,400$ times.

In the 2D Fourier domain, the spectral consequences of this operation can be appreciated by examining the 2D Fourier Transform of the convolution kernel above. The kernel is equivalent to the superposition of two centered square box functions, one of size (8×8) and amplitude −1, and the other of size (4×4) and amplitude +4 (for the central region in which they overlap, the two therefore sum to +3). The 2D Fourier Transform of each of these square functions is a 2D "sinc" function, whose size parameters differ by a factor of two in each of the dimensions and whose amplitudes are equal but opposite, because the two component boxes have equal but opposite volumes. Thus, the overall kernel has a 2D Fourier Transform $K(\mu,v)$ which is the difference of two differently-sized 2D sinc functions, as given by equation 4.

$$K(\mu, v) = \frac{\sin(\mu)\sin(v)}{\pi^2 \mu v} - \frac{\sin(2\mu)\sin(2v)}{4\pi^2 \mu v} \quad (4)$$

This is a high-pass (or ultimately a band-pass) filter, selecting only a high range of spatial frequencies in all orientations. Towards its center, corresponding to very low spatial frequencies, its value approaches zero (as can also be inferred from the fact that the sum of all pixel weights in the convolution kernel shown above is zero). Thus, low frequencies play little or no role in computing a focus score, and only relatively high frequencies contribute significantly to the computation of a focus score. Equation (3) shows that summing the squares of all the local convolution sums across the image is equivalent to summing the total amount of high frequency energy in the 2D Fourier Transform of the image. The action of the convolution kernel is to impose the above power spectral weighting function so that primarily high frequency energy is measured.

Finally, the summated 2D spectral energy is passed through a compressive nonlinearity of the form $f(x)=100 x^2/(x^2+c^2)$ in order to generate a normalized focus score in the range of 0 to 100 for any image.

The focus assessment technique is applied immediately after each image frame is digitized and stored in the frame buffer memory 410 in order to assess whether the focus quality is sufficient to warrant any further processing. If the calculated focus quality value of the captured image is greater than or equal to a predetermined value, the image is passed to applicable programs for further processing, for example for extraction of a biometric template. The focus assessment technique can be used to compare the relative focus of an entire series of images in order to select the one most in-focus (i.e. having the highest focus assessment score), as well as to measure a single image.

The focus assessment technique can be used to provide a feedback indication to a system user who controls the position of the imager relative to the object being imaged. This can be accomplished by activating an indicator which would continue, while successive images are captured and their focus assessed, until the focus assessment score exceeds a predetermined value. At this point, the indicator is deactivated and the last image captured is transferred to the image processor 210 where it is processed to extract the biometric template.

The application of the focus assessment technique in combination with the feedback indicator helps resolve the man-machine interface problems associated with the use of digital imaging devices on the eye. Individuals using the system are provided positive, objective indicators and feedback as to the quality of image focus. The focus assessment processor can also be used in any situation where it is required to determine the quality of focus of video images at industry standard frame rates (NTSC and PAL).

Thus, the image is obtained at the imager and transmitted to an analog to digital converter 405. The digitized video information is then stored in a frame buffer memory 410. The focus assessment processor 420 isolates the central 320×320 region of the image. 8×8 pixel blocks (each pixel is in only one block) are then processed by first summing pixels in the central 4×4 region, tripling that sum, and then subtracting from this value all the pixel values in the outer two pairs of rows and columns. This result is then squared. This process is performed on each 8×8 block, and the results are summed. After the entire image has been processed, the summed result is compressed nonlinearly to generate a focus score between 0 and 100. This score is then compared to a predetermined number for determining if the indicator 310 should be activated.

Figure 9:
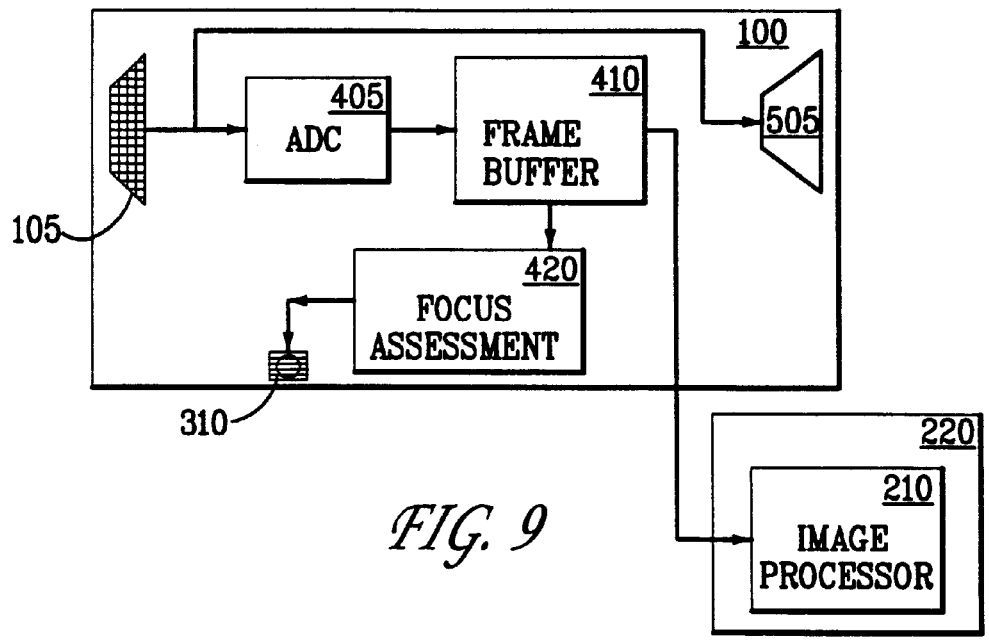
FIG. 9 is a schematic diagram of an exemplary iris imager comprising a focus assessment processor in accordance with the present invention.

The focus assessment can be performed by the microprocessor 210 in the computer 200, or it can be a separate processor element. For example, the focus assessment processor 420 can be disposed within the handheld imager 100, as shown in FIG. 9, and not be external to the imager 100, as shown in FIG. 8. A benefit of this embodiment is that the selection of a properly focused image can occur within the hand-held device, so that only a single, acceptable image is transmitted to the external processor 210. In the embodiment shown in FIG. 8, the focus assessment algorithm is typically performed within a personal computer, so digitized image data is transmitted to the personal computer at video rates. However, the high data rates associated with transmission of digitized video cannot be supported by some types of computers, particularly notebook-style personal computers. If the focus assessment is performed in the handheld device 100, the single selected video frame can then be transmitted at a lower data rate which is compatible with notebook-style personal computers. This greatly enhances the flexibility and versatility of the handheld imaging device of the present invention.

As shown in FIG. 9, the video signal (analog) from the camera 105 is converted to digital format by an analog-to-digital converter 405 and each frame of video is stored in a frame buffer memory 410. The converter 405 and memory 410 are similar to those described above with respect to FIG. 8, but are disposed within the handheld imager 100. Data in the frame buffer 410 is processed by a focus assessment processor 420 which is also contained within the handheld imager 100. The results of the focus assessment control an audible indicator 310 which emits a sound that is discontinued when an acceptable video frame is acquired. The single video frame that has been determined to be acceptable is transmitted to another processor 210 (typically within a personal computer 200) for further processing and comparison.

It is contemplated that in addition to the focus assessment processor, an auto-focus lens system could be used in the present invention. The results of the focus assessment control the lens system, thereby automatically adjusting focus to produce an optimal image. This would place less of a premium on the accuracy with which the user positions the eye, and would be helpful if the user could not see or hear the indicators described above.

Optionally, the imager of the present invention can be equipped with a display, such as a miniaturized back-illuminated liquid crystal display (LCD) 505. The LCD display 505 is disposed on the side of the imaging system opposite the subject whose eye is being imaged. The video signal generated by the camera 105 is continuously displayed on the LCD display 505 to permit an operator (other than the subject whose eye is being imaged) to control the position of the hand-held imaging device 100 and thereby center the eye's image in the field of view to more easily achieve proper focus, as indicated by the sound emitted by the audible indicator 310. This allows the device to be used on individuals who are unable or unwilling to cooperate in the image acquisition process. Thus, in accordance with the present invention, either a user can scan his own iris (e.g., for entry to a building) or a user can scan another subject's iris (e.g., for identification).

Figure 10:
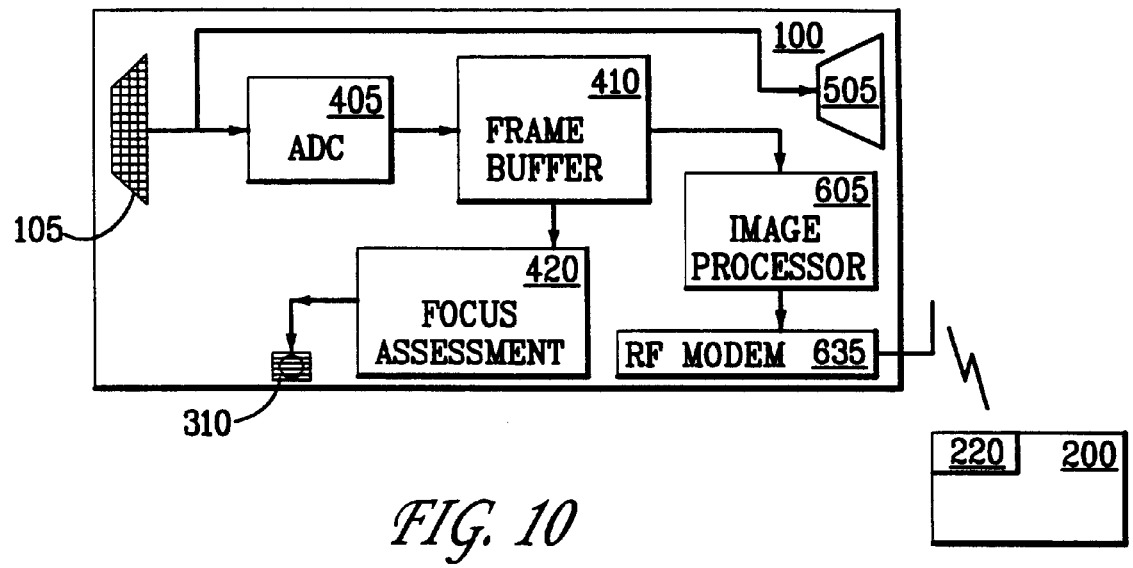
FIG. 10 is a schematic diagram of an exemplary iris imager comprising a focus assessment processor and image processor in accordance with the present invention.

An additional embodiment of the present invention is shown in FIG. 10. In FIG. 10, an additional processor 605 has been added to the device of FIG. 9. The additional processor 605 extracts the iris image data, processes it to produce a biometric template, and encrypts it so that the output of the handheld imager 100 is an encrypted biometric template that can be used by the processor 210 in the computer 200 for comparison. Encryption can be with any of the known encryption techniques using public and private keys to encipher and decipher the data, respectively. One advantage offered by this embodiment of the invention is that the added functionality required to add the biometric identification technology to a computer system is contained within the handheld imager 100, thereby simplifying installation, support, and service. Secondly, the security of transactions which utilize the biometric template is enhanced because the data is generated and encrypted totally external to the computer 200 and thus is less susceptible to theft, alteration, or interception.

In the embodiment of FIG. 10, a wireless modem 635, similar to the modem 135 described above with respect to FIG. 5, is shown. The encrypted biometric template from the processor 605 is transmitted via the modem 635 to the computer 200 for further processing and comparison. The modem 635 also receives instructions from the computer 200, such as to activate visible and/or audible indicators.

Some applications that can use the imager of the present invention are bank automated teller machines, computer workstations, and handicapped equipped access points. Also, a store clerk could verify identity for a credit card transaction, or a customs agent could verify identity.

Although illustrated and described herein with reference to certain specific embodiments, it will be understood by those skilled in the art that the invention is not limited to the embodiments specifically disclosed herein. Those skilled in the art also will appreciate that many other variations of the specific embodiments described herein are intended to be within the scope of the invention as defined by the following claims.

What is claimed is:

1. A handheld iris imaging apparatus for obtaining an image of an iris of an eye, comprising:

iris acquisition means having a front surface;

a lens having an image plane disposed in front of said front surface of said iris acquisition means;

a concave cold mirror disposed on a side of said lens opposite said iris acquisition means; and an illuminator disposed along a side of said mirror.

2. The iris imaging apparatus according to claim 1, wherein said iris acquisition means comprises a camera.

3. The iris imaging apparatus according to claim 2, wherein said camera is sensitive to light having a wavelength in a range between about 400 nm and about 1100 nm.

4. The iris imaging apparatus according to claim 2, wherein said mirror reflects light having a wavelength in a range between about 400 nm and about 700 nm and passes light having a wavelength greater than about 700 nm.

5. The iris imaging apparatus according to claim 1, wherein said illuminator emits light having a wavelength in a range between about 680 nm and about 900 nm towards the iris of the eye being imaged, the eye being out of contact with the iris imaging apparatus.

6. The iris imaging apparatus according to claim 1, further comprising at least one of a visible indicator and an audible indicator to indicate when the image of the iris has been obtained.

7. A system of identification, comprising:

the handheld iris imaging apparatus of claim 1;

a first memory for storing at least one template of at least one image of an iris of at least one person's eye;

a second memory for storing a template of an iris image obtained by said iris acquisition means; and a comparator for comparing said template of said iris image of said second memory with said at least one stored template of said first memory to identify the person.

8. The system according to claim 7, wherein said iris acquisition means comprises a camera.

9. The system according to claim 8, wherein said comparator comprises a processor responsive to an output of said camera for comparing said template of said iris image of said second memory with said at least one stored template of said first memory.

10. The system according to claim 7, wherein said first memory, said second memory, and said comparator are disposed in a housing that is separate from said handheld iris imaging apparatus.

11. The system according to claim 10, wherein said housing is coupled to said handheld iris imaging apparatus by a wireless modem.

12. The system according to claim 7, further comprising at least one of a visible indicator and an audible indicator disposed within said handheld iris imaging apparatus.

13. The system according to claim 12, further comprising a focus assessment processor coupled to said at least one of a visible indicator and an audible indicator.

14. The system according to claim 7, further comprising a display disposed within said handheld iris imaging apparatus.

15. A method of obtaining an iris image of a subject, comprising the steps of:
   (a) illuminating an iris of the subject;
   (b) forming an approximately centered image of said iris at an image plane of a camera using a concave cold mirror;
   (c) storing said image in a memory;
   (d) determining if said image is an image having a focus quality greater than or approximately equal to a predetermined threshold; and
   (e) repeating steps (a) through (d) until said image having a focus quality greater than or approximately equal to the predetermined threshold is obtained.

16. The method according to claim 15, further comprising the step of activating an indicator if said image has a focus quality less than the predetermined threshold.

17. The method according to claim 15, further comprising the step of activating an indicator if said image has a focus quality greater than or approximately equal to the predetermined threshold.

18. The method according to claim 15, further comprising the step of displaying said image on a display.

19. The method according to claim 15, wherein said step of forming said approximately centered image of said iris comprises forming said approximately centered image responsive to at least one of focus information and positioning information provided by said concave cold mirror.

20. A method of identification of a person, comprising the steps of:
   (a) storing image information of the iris of at least one person's eye;
   (b) illuminating an eye of an unidentified person having an iris;
   (c) obtaining an image of said iris of said unidentified person using a concave cold mirror;
   (d) storing said image in a memory;
   (e) determining if said image is an image having a focus quality greater than or approximately equal to a predetermined threshold for a step (g) of comparing;
   (f) repeating steps (b) through (e) until said image having a focus quality greater than or approximately equal to the predetermined threshold is obtained; and
   (g) comparing a template of said obtained image with said stored image information to identify said unidentified person.

21. The method according to claim 20, further comprising the step of activating an indicator if said image has a focus quality less than the predetermined threshold.

22. The method according to claim 20, further comprising the step of activating an indicator if said image has a focus quality greater than or approximately equal to the predetermined threshold.

23. The method according to claim 20, wherein said step of determining if said image is an image having a focus quality greater than or approximately equal to the predetermined threshold comprises the step of focus assessment processing said image.

24. The method according to claim 20, further comprising the step of displaying said image on a display.

25. The method according to claim 20, wherein said step of obtaining said image of said iris comprises obtaining said image responsive to at least one of focus information and positioning information provided by said concave cold mirror.

* * * * *